United States Patent [19]

Liang

[11] 4,341,795
[45] Jul. 27, 1982

[54] ASYMMETRICAL BIS-CARBAMATE COMPOUNDS

[75] Inventor: Wei C. Liang, South Charleston, W. Va.

[73] Assignee: Union Carbide Corporation, Danbury, Conn.

[21] Appl. No.: 636,623

[22] Filed: Dec. 1, 1975

[51] Int. Cl.³ ............... A01N 47/12; C07C 153/00
[52] U.S. Cl. ................................. 424/300; 424/246; 424/263; 424/267; 424/274; 424/275; 424/276; 424/277; 424/278; 424/283; 424/285; 544/58.2; 546/244; 546/331; 549/21; 549/29; 549/38; 549/51; 549/76; 549/77; 260/326.2; 260/340.6; 260/340.9 R; 260/345.8 R; 260/347.2; 260/453.3 R; 260/465 A; 260/465.4; 560/134; 560/135; 560/136; 560/137

[58] Field of Search .............. 424/300, 246, 263, 267, 424/274, 275, 276, 277, 278, 283, 285; 260/481 C, 326.2, 340.6, 340.9 R, 345.8 R, 347.2, 453.3 R, 465 A, 465.4; 544/58.2; 546/331, 244; 549/21, 29, 38, 51, 76, 77; 560/134, 135, 136, 137

[56] References Cited

U.S. PATENT DOCUMENTS 3,679,733 7/1972 Brown .................................. 560/134
3,794,733 2/1974 Brown .................................. 424/263
3,812,174 5/1974 Brown et al. ................. 260/239.3 R Primary Examiner—Henry R. Jiles
Assistant Examiner—Bernard Dentz
Attorney, Agent, or Firm—Clement J. Vicari; William R. Moran; Robert C. Brown

[57] ABSTRACT

Asymmetrical N-substituted bis-carbamoyl sulfide compounds exhibit exceptional broad spectrum pesticidal activity coupled with extremely low mammalian toxicity and phytotoxicity.

54 Claims, No Drawings

ASYMMETRICAL BIS-CARBAMATE COMPOUNDS

This invention relates to methods and compositions for controlling insect and acaricidal pests. In another aspect this invention relates to asymmetrical N-substituted bis-carbamoyl sulfide compounds which are themselves novel and to their production.

The compounds which are employed as the active ingredients in the pesticidal compositions of this invention are asymmetrical bis-carbamoyl sulfide compounds of the following general formula:

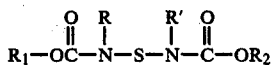

wherein:
R and R' are individually alkyl radicals having from 1 to 4 carbon atoms;
$R_1$ is: naphthyl, benzothienyl, benzofuranyl or:

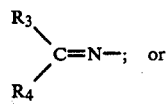

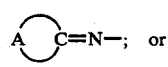

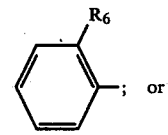

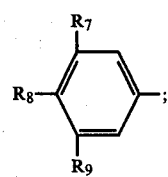

$R_2$ is other than $R_1$ and X is substituted or unsubstituted alkyl, cycloalkyl, phenylalkyl, naphthylalkyl or a heterocycloalkyl group wherein the heterocyclic moiety is a five-or six-member ring which includes in any combination, one or two oxygen, sulfur, sulfinyl or sulfonyl groups and which may also include one divalent amino, alkylamino or carbonyl group; wherein the permissable substituents on said groups are one or more halogen, nitrile, nitro, alkyl, alkylthio, alkylsulfinyl, alkylsulfonyl, alkoxy, alkoxycarbonylamino, or alkylcarbonylamino groups in any combination, or $R_2$ is alkoxyalkyleneoxyalkyl, alkoxy(dialkyleneoxy)alkyl or alkoxy(trialkyleneoxy)alkyl; with the proviso that except where $R_2$ is alkyl, no single alkyl or alkylene moiety in any $R_2$ group may include more than six carbon atoms;
$R_3$ is hydrogen, alkyl, alkylthio or cyano;
$R_4$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or $R_4$ is phenyl, aminocarbonyl, alkylaminocarbonyl, dialkylaminocarbonyl or a $R_5CONH-$ or $R_5CON(alkyl)-$ group, where $R_5$ is hydrogen, alkyl, alkoxy or alkylthio; and
A is a divalent aliphatic chain, completing a five or six member ring, which includes in any combination, one or two oxygen, sulfur, sulfinyl or sulfonyl groups and which may also include one divalent amino, alkylamino or carbonyl group;
$R_6$ is alkoxy, alkylthio, alkyl, alkylthioalkyl, 2-dioxolanyl or halogen; or
$R_7$ is alkyl;
$R_8$ is hydrogen, alkyl, halogen, alkylthio, alkylsulfinyl, alkylsulfonyl, alkoxy, dialkylamino, formylamino, alkylcarbonylamino, alkoxycarbonylamino or dialkylaminomethyleneimino;
$R_9$ is hydrogen or alkyl;
with the proviso that the number of aliphatic carbon atoms in $R_3$, $R_4$, A, $R_6$, $R_7$, $R_8$ and $R_9$, individually, may not exceed eight.

The preferred compounds of this invention are those in which R and R' are methyl. Also preferred are those compounds wherein $R_1$ is:

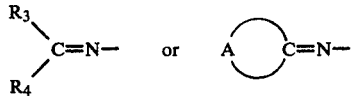

The active compounds of this invention exhibit a very high level of pesticidal activity coupled with substantially reduced mammalian toxicity and plant phytotoxicity as compared with other known pesticidal compounds having a comparable spectrum of activity against insect and arachnid pests.

The asymmetrical bis-carbamoyl sulfides of this invention can be prepared conveniently by the method shown in the following general reaction scheme:

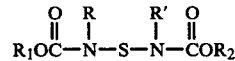

wherein R, R', $R_1$ and $R_2$ are as defined above.

One equivalent of an oxime or hydroxyl reactant ($R_1OH$ or $R_2OH$ reactant) is reacted with a carbamate-carbamoyl fluoride starting reactant in the presence of at least one equivalent of an acid acceptor, preferably in an inert solvent, to produce the desired asymmetrical bis-carbamate compound. The carbamate-carbamoyl fluoride starting reactants can be prepared by the method illustrated by the following general reaction scheme:

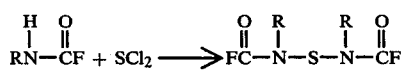

-continued

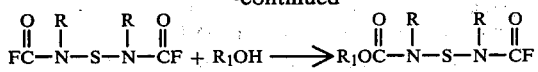

This procedure is particularly useful for the production of compounds according to the invention where R and R' are the same. In this procedure hydrogen fluoride is reacted with an alkylisocyanate compound to form an alkylaminocarbonylfluoride compound which is then reacted with sulfur dichloride in the presence of at least two equivalents of an acid acceptor, preferably in an inert solvent, to yield bis-(N-alkyl-N-fluorocarbonylamino) sulfide. The bis-sulfide compound is then reacted with a hydroxyl or oxime ($R_1OH$ or $R_2OH$) compound in the presence of at least one equivalent of an acid acceptor and preferably in the presence of an inert solvent, to yield the desired carbamate-carbamoyl fluoride compound.

An alternative procedure for preparing the carbamate-carbamoyl fluoride starting material employed in procedure I above is illustrated by the following general reaction scheme:

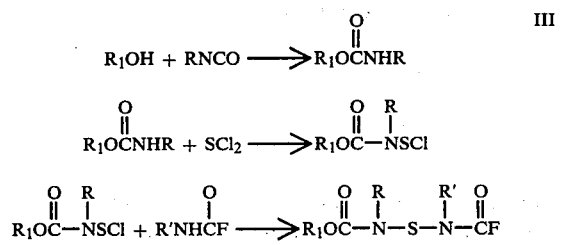

This procedure may be employed when it is desired to produce compounds according to the invention wherein R and R' are different. In this procedure a hydroxyl or oxime compound ($R_2OH$ may be used in place of $R_1OH$) is reacted with an alkylisocyanate to form the corresponding $R_1$ or $R_2$-oxycarbonylaminoalkyl compound which is then reacted with sulfur dichloride in the presence of at least two equivalents of an acid acceptor and preferably in the presence of an inert solvent to yield a chlorosulfenyl compound as shown above. The chlorosulfenyl compound is then reacted with an alkylaminocarbonyl fluoride compound to produce the carbamate-carbamoyl fluoride starting reactant employed in procedure I above. It will be understood that an $R_2$ carbamate-carbamoyl fluoride will be prepared if $R_2OH$ is substituted for $R_1OH$ in procedures II and III. It will also be understood that compounds according to this invention can be prepared by reacting an $R_2$ carbamate-carbamoyl fluoride with $R_1OH$ reactant in accordance with procedure I above.

The production of the starting carbamate-carbamoyl fluoride compounds is described more fully in my copending U.S. patent application Ser. No. 636,371 filed concurrently herewith entitled "Carbamate-Carbamoyl Fluoride Compounds".

The acid acceptor employed in the above reactions can be either an organic or inorganic base such as triethylamine or sodium or potassium hydroxide. A phase transfer agent such as a crown ether may also be employed. Any conventional inert solvent, such as benzene, toluene, dioxane, tetrahydrofuran, ethylether, methylene chloride or the like can be used in the conduct of these reactions.

These reactions may also be carried out in a two-phase system such as an aqueous solution of an inorganic base as one phase and an aromatic solvent including a quaternary ammonium salt as a phase transfer agent as the second phase. The reaction temperature is not critical in these procedures. The reactions go essentially to completion at room temperature. Elevated temperatures may be employed if it is desired to reduce reaction time. These reactions are preferably carried out at temperatures ranging from 10° to 50° C.

The hydroxyl and oxime reactants ($R_1OH$ and $R_2OH$) employed in the procedures described above, are known classes of compounds which can be prepared by conventional methods. See for example U.S. Pat. Nos. 3,752,841; 3,726,908; 3,843,669 and Belgian Pat. Nos. 813,206 and 815,513.

The following compounds are representative of the novel compounds of this invention:

S-Methyl-N-[N'-(N''-methyl-N''-(methoxycarbonyl)aminosulfenyl)-N'-methylcarbamoyloxy]thioacetimidate S-Methyl-N-[N'-(N'-methyl-N''-(ethoxycarbonyl)aminosulfenyl)-N'-methylcarbamoyloxy]thioacetimidate S-Methyl-N-[N'-(N''-methyl-N''-(butoxycarbonyl)aminosulfenyl-N'-methylcarbamoyloxy]thioacetimidate S-Methyl-N-[N'-(N''-methyl-N''-(t-butoxycarbonyl)aminosulfenyl)-N'-methylcarbamoyloxy]thioacetimidate S-Methyl-N-[N'-(N''-methyl-N''-(2-ethylhexyloxycarbonyl)aminosulfenyl)-N'-methylcarbamoyloxy]thioacetimidate S-Methyl-N-[N''-methyl-N''-(n-dodecyloxycarbonyl)aminosulfenyl)-N'-methyl carbamoyloxy]thioacetimidate S-Methyl-N-[N'-(N''-methyl-N'-(n-octadecyloxycarbonyl)aminosulfenyl)-N'-methylcarbamoyloxy]thioacetimidate S-Methyl-N-[N'-(N''-methyl-N''-(benzyloxycarbonyl)aminosulfenyl)-N'-methylcarbamoyloxy]thioacetimidate S-Methyl-N-[N'-(N'-methyl-N''-(2-methoxyethoxycarbonyl)aminosulfenyl)-N'-methylcarbamoyloxy]thioacetimidate S-Methyl-N-[N'-(N''-methyl-N''-(2-(2-methoxyethoxy)ethoxycarbonyl)aminosulfenyl)-N'-methylcarbamoyloxy]thioacetimidate S-Methyl-N-[N'-(N''-methyl-N''-(2-(2-(2-methoxyethoxy)ethoxy) ethoxycarbonyl)aminosulfenyl)-N'-methylcarbamoyloxy]thioacetimidate S-Methyl-N-[N'-(N''-methyl-N''-(2-n-hexyloxyethoxycarbonyl) aminosulfenyl)-N'-methylcarbamoyloxy]-thioacetimidate S-Methyl-N-[N''-methyl-N''-(2-(2-n-hexyloxyethoxy)ethoxycarbonyl)aminosulfenyl)-N'-methylcarbamoyloxy]thioacetimidate 5-Methyl-4-[[O-[N-methyl-N-(N'-methyl-N'-(ethoxycarbonylaminosulfenyl)carbamoyl]oximino]]-1,3oxathiolane 5-Methyl-4-[[O-[N-methyl-N-(N'-methyl-N'-(n-dodecyloxycarbonylaminosulfenyl)carbamoyl]oximino]]-1,3-oxathiolane 5,5-Dimethyl-4-[[O-[N-methyl-N-(N'-methyl-N'-(t-butoxycarbonylaminosulfenyl)carbamoyl]oximino]]-1,3-dithiolane 5,5-Dimethyl-4-[[O-[N-methyl-N-(N'-methyl-N-(n-dodecyloxycarbonylaminosulfenyl)carbamoyl]oximino]]-1,3-dithiolane 2-[[O-[N-Methyl-N-(N'-methyl-N'-(ethoxycarbonylaminosulfenyl)carbamoyl]oximino]]-1,4-dithiane 2-[[O-[N-Methyl-N-(N'-methyl-N'-(n-octadecyloxycarbonylaminosulfenyl)carbamoyl)oximino]]-1,4-dithiane S-2-Cyanoethylthio-N-[N'-(N''-methyl-N''-(ethoxycarbonyl)aminosulfenyl-N'-methylcarbamoyloxy]thioacetimidate S-2-Cyanoethylthio-N-[-N'-(N'-(N''-methyl-N''-(n-dodecyloxycarbonyl)aminosulfenyl)-N'-methylcarbamoyloxy]thioacetimidate S-Isopropyl-N-[N'-(N''-methyl-N''-(ethoxycarbonyl)aminosulfenyl)N'-methylcarbamoyloxy]thioacetimidate S-Isopropyl-N-[N'-(N''-methyl-N''-(2-methoxyethoxycarbonylaminosulfenyl)-N'-methylcarbamoyloxy]thioacetimidate 2,3-Dihydro-2,2-dimethyl-7-benzofuranyl-N-[N'-(ethoxycarbonyl)-N'-methylaminosulfenyl]N-methylcarbamate 2,3-Dihydro-2,2-dimethyl-7-benzofuranyl-N-[N'(t-butoxycarbonyl)N'-methylaminosulfenyl]-N-methylcarbamate 1-Naphthyl-N-methyl-N-[N'-(ethoxycarbonyl)-N'-methylaminosulfenyl]carbamate O-Methyl-2-isopropyl-4-[N-(N'-ethoxycarbonyl)-N'-methylaminosulfenyl)-N-methylcarbamoyloxy]carbanilate O-Methyl-2,6-dimethyl-4-[N-(N'-(ethoxycarbonyl)-N'-methylaminosulfenyl)-N-methylcarbamoyloxy]carbanilate O-[N-(N'-(2-Acetamidoethoxycarbonyl)-N'-butylaminosulfenyl)-N-methylcarbamoyl]-S-ethylacetothiolhydroximate O-[N-(N'-(2-Formamidopropycarbonyl)-N'-methylaminosulfenyl)-N-methylcarbamoyl]-S-cyanomethylacetothiolhydroximate O-[N-[N'-(2-Methoxycarbonylaminocyclohexyloxycarbonyl)-N-isopropylaminosulfenyl)-N-methylcarbamoyl]-S-methylacetothiolhydroximate O-[N-[N'-(2-Methylsulfonyl-2-methylpropoxycarbonyl)-N'-methylaminosulfenyl)-N-methylcarbamoyl]-S-methylacetothiolhydroximate O-[N-[N'-(2-Ethylsulfinylbutoxycarbonyl)-N'-ethylaminosulfenyl)-N-ethylcarbamoyl]-S-methylacetothiolhydroximate O-[N-(N'-(1-Naphthylmethoxycarbonyl)-N'-methylaminosulfenyl)-N-methylcarbamoyl]-S-methylacetothiolhydroximate O-[N-(N'-Cyclopentyloxycarbonyl-N'-methylaminosulfenyl)-N-methylcarbamoyl]-S-methylacetothiolhydroximate O-[N-(N'-Cyclohexyloxycarbonyl-N'-methylaminosulfenyl)-N-methylcarbamoyl]-S-methylacetothiolhydroximate O-[N-(N'-o-Chlorobenzyloxycarbonyl-N'-methylaminosulfenyl)-N-methylcarbamoyl]-S-methylacetothiolhydroximate O-[N-(N'-m-Chlorobenzyloxycarbonyl-N'-methylaminosulfenyl)-N-methylcarbamoyl]-S-methylacetothiolhydroximate O-[N-(N'-p-Chlorobenzyloxycarbonyl-N'-methylaminosulfenyl)-N-methylcarbamoyl]-S-methylacetothiolhydroximate O-[N-(N'-o-Methoxybenzyloxycarbonyl-N'-methylaminosulfenyl)-N-methylcarbamoyl]-S-ethylacetothiolhydroximate O-[N-(N'-m-Metoxybenzyloxycarbonyl-N'-methylaminosulfenyl)-N-methylcarbamoyl]-S-propylacetothiolhydroximate O-[N-(N'-p-Methoxybenzyloxycarbonyl-N'-methylaminosulfenyl)-N-methylcarbamoyl]-S-(2-cyanoethyl)acetothiolhydroximate O-[N-(N'-o-Nitrobenzyloxycarbonyl-N'-methylaminosulfenyl)-N-methylcarbamoyl]-S-methylacetothiolhydroxime O-[N-(N'-m-Nitrobenzyloxycarbonyl-N'-methylaminosulfenyl)-N-methycarbamoyl]-S-isopropylacetothiolhydroximate O-[N-(N'-p-Nitrobenzyloxycarbonyl-N'-methylaminosulfenyl)-N-methylcarbamoyl]-S-methylacetothiolhydroximate O-[N-(N'-Furfuryloxycarbonyl-N'-methylaminosulfenyl)-N-methylcarbamoyl]-S-methylacetothiolhydroximate O-[N-(N'-2-Pyridylmethyloxycarbonyl-N'-methylaminosulfenyl)-N-methylcarbamoyl]-S-ethylacetothiolhydroximate O-[N-(N'-2-Thiophenemethyloxycarbonyl-N'-methylaminosulfenyl)-N-methylcarbamoyl]-S-methylacetothiolhydroximate 3-Chlorophenyl N-[N'-methyl-N'-(2-chloroethoxycarbonyl)aminosulfenyl]-N-methylcarbamate 2-Isopropoxyphenyl N-[[N'-[2-(N''-methylacetamido)ethoxycarbonyl]-N'-butylaminosulfenyl]]-N-methylcarbamate 3,5-Dimethyl-4-methylthiophenyl N-[N'-propyl-N'-(2,2,2-trichloroethoxycarbonyl)aminosulfenyl]-N-methylcarbamate 3,5-Dimethylphenyl N-[N'-methyl-N'-(2,2,2-trichloroethoxycarbamoyl)aminosulfenyl]-N-methylcarbamate 3,5-Dimethyl-4-methylsulfinylphenyl N-[N'-methyl-N'-(2,2,2-trichloroethoxycarbonyl)aminosulfenyl]-N-methylcarbamate 3,5-Dimethyl-4-methylsulfonylphenyl N-[N'-methyl-N'-(2-methylthioethoxycarbonyl)aminosulfenyl]-N-methylcarbamate 3,5-Dimethyl-4-N,N-dimethylaminophenyl N'-[N''-methyl-N''-(2-nitrobenzyloxycarbonyl)aminosulfenyl]-N'-methylcarbamate 3,5-Dimethyl-4-acetamidophenyl N-[N'-methyl-N'-(2-methylsulfinylethoxycarbonyl)aminosulfenyl]-N-methylcarbamate 3-Methyl-4-(dimethylaminomethyleneimino)phenyl N-[N'-methyl-N'-(2-methylsulfonylethoxycarbonyl)aminosulfenyl]-N-methylcarbamate 3-Isopropyl-4-formoaminophenyl N-[N'-ethyl-N'-(2-cyanoethoxycarbonyl)aminosulfenyl]-N-methylcarbamate 3-Isopropylphenyl N-[N'-methyl-N'-(2-nitroethoxycarbonyl)aminosulfenyl]-N-methylcarbamate 2-[N-[N'-(cyclohexyloxycarbonyl)-N'-methylaminosulfenyl]-N-methylcarbamoyloxyimino]-4-methyl-1,4-tetrahydrothiazin-3-one 2-[N-[N'-(cyclopentyloxycarbonyl)-N'-methylaminosulfenyl]-N-methylcarbamoyloxyimino]-1,4-tetrahydrothiazin-3-one O-[N-(N'-(3,4-Dichlorobenzyloxycarbonyl)-N'-methylaminosulfenyl)-N-methylcarbamoyl]-S-methyl-1-(dimethylaminocarbonyl)formothiolhydroximate O-[N-(N'-(4-t-Butylbenzyloxycarbonyl]-N'-methylaminosulfenyl)-N-methylcarbamoyl]-S-methyl-1-(methylaminocarbonyl)formothiolhydroximate O-[N-(N'-(3-methylthiobenzyloxycarbonyl)-N'-methylaminosulfenyl)-N-methylcarbamoyl]-S-methyl-1-(aminocarbonyl)formothiolhydroximate 2,6-Di-t-butyl-4-(2',2'-dicyanoethylidenyl)phenyl N-[N'-methyl-N'-(cyclohexyloxycarbonyl)aminosulfenyl]-N-methylcarbamate O-[N-[N'-Methyl-N'-(butoxycarbonyl)aminosulfenyl]-N-methylcarbamoyl]-2-methyl-2-cyano-propionaldoxime O-[N-[N'-Methyl-N'-(propoxycarbonyl)aminosulfenyl]-N-methylcarbamoyl]-2-methyl-2-(methylthio)-propionaldeoxime O-[N-[N'-Methyl-N'-(ethoxycarbonyl)aminosulfenyl]-N-methylcarbamoyl]-2-methyl-2-nitro-propionaldoxime O-[N-[N'-Methyl-N'-(methoxycarbonyl)aminosulfenyl]-N-methylcarbamoyl]-2-methyl-2-methylsulfinyl-propionaldoxime O-[N-[N'-Methyl-N'-(2-ethylhexyloxycarbonyl)aminosulfenyl]-N-methylcarbamoyl]-2-methyl-2-methylsulfonyl-propionaldoxime O-[N-[N'-Methyl-N'-(n-octyloxycarbonyl)aminosulfenyl]-N-methylcarbamoyl]-2-methyl-2-formamido-propionaldoxime O-[N-[N'-Methyl-N'-(n-dodecyloxycarbonyl)aminosulfenyl]-N-methylcarbamoyl]-2-methyl-2-acetamido-propionaldoxime O-[N-(N'-Methyl-N'-(2-ethylhexyloxycarbonyl)aminosulfenyl)-N-methylcarbamoyl]-1-cyano-1-(t-butyl)formohydroximate O-[N-[N'-(Butoxycarbonyl)-N'-methylaminosulfenyl]-N-methylcarbamoyl]-1-(methylthio)-3,3-dimethyl-2-butanone oxime O-[N'-[N'-(2-Ethylhexyloxycarbonyl)-N'-methylaminosulfenyl]-N-methylcarbamoyl]-1-(methylthio)-3,3-dimethyl-2-butanone oxime O-[N-[N'-(n-Octyloxycarbonyl)-N'-methylaminosulfenyl]-N-methylcarbamoyl]-1-(methylsulfinyl)-3,3-dimethyl-2-butanone oxime O-[N-[N'-(n-Pentoxycarbonyl)-N'-methylaminosulfenyl]-N-methylcarbamoyl]-1-(methylsulfonyl)-3,3-dimethyl-2-butanone oxime O-[N-[N'-(Butoxycarbonyl)-N'-methylaminosulfenyl]-N-methylcarbamoyl]-3-(methylsulfonyl)-2-butanone oxime The following examples are provided to more clearly illustrate the manner in which the new compounds of this invention may be prepared.

EXAMPLE I

Preparation of
S-Methyl-N-[N'-(N''-Methyl-N''-(Ethoxycarbonyl)Aminosulfenyl)-N'-Methylcarbamoyloxy]Thioacetimidate A mixture of powdered potassium hydroxide (4.71 g., 0.07 mole), 1-methylthioacetaldoxime (7.49 g., 0.07 mole) and 0.1 g. of dicyclohexyl-18-crown-6 in 200 ml. of benzene was stirred at room temperature for 0.75 hr. To this mixture was added a solution of 15 g. (0.07 mole) of N-(N'-ethoxycarbonyl-N'-methylaminosulfenyl)-N-methylcarbamoyl fluoride at 25° to 30° C. After stirring for an additional 2.5 hr., the mixture was washed with water until the washings became neutral. The benzene solution was dried over anhydrous magnesium sulfate, filtered and concentrated to give 15 g. of residue. The residue was extracted with hexane. The yellow solid S-Methyl-N-[N'-(N''-methyl-N''-(ethoxycarbonyl)aminosulfenyl)-N'-methylcarbamoyloxy]thioacetimidate (7.0 g.) was recrystallized from diisopropyl ether to give 6.6 g. of product, mp 64°–65° C.

Anal. Calcd for $C_9H_{17}N_3O_4S_2$: C, 36.60; H, 5.80; N, 14.23. Found: C, 36.63; H, 5.62; N, 14.24.

EXAMPLE II

Preparation of
S-Methyl-N-[N'-(N''-Methyl-N''-(Butoxycarbonyl)Aminosulfenyl)-N'-Methylcarbamoyloxy]Thioacetimidate A solution of 11.9 g. (0.05 mole) of N-(N'-butoxycarbonyl-N'-methylaminosulfenyl)-N-methylcarbamoyl fluoride, 5.25 g. (0.05 mole) of 1-methylthioacetaldoxime and 5.57 g. (0.055 mole) of triethylamine in 200 ml of 1,4-dioxane was stirred at ambient temperature for 72 hr. The mixture was then poured into 800 ml of water and was extracted with four 150 ml portions of ethyl acetate. The combined ethyl acetate extracts were washed with a saturated aqueous sodium bicarbonate solution, then with water until neutral, dried over anhydrous magnesium sulfate, filtered, and concentrated to yield 14.6 g. residue (90%). A small amount was chromatographed through a silica gel packed column. After recrystallization from diisopropyl ether, white crystalline solid S-Methyl-N-[N'-(N''-methyl-N''-(butoxycarbonyl)aminosulfenyl)-N'-methylcarbamoyloxy]thioacetimidate was obtained m.p. 51.5°–52.5° C.

Anal. Calcd for $C_{11}H_{21}N_3O_4S_2$: C, 40.85; H, 6.55; N, 12.99. Found: C, 40.75; H, 6.61; N, 13.01.

EXAMPLE III

Preparation of
S-Methyl-N-[N'-(N''-Methyl-N''-(t-Butoxycarbonyl)Aminosulfenyl)-N'-Methylcarbamoyloxy]Thioacetimidate A solution of 11.9 g (0.05 mole) of N-(N'-t-butoxycarbonyl-N'-methylaminosulfenyl)-N-methylcarbamoyl fluoride, 5.25 g (0.05 mole) of 1-methylthioacetaldoxime and 6.07 g (0.6 mole) of triethylamine in 200 ml of 1,4-dioxane was stirred at ambient temperature for 48 hr. The mixture was then poured into 800 ml of water and was extracted with four 150 ml portions of ethyl acetate. The combined extracts were washed with 100 ml of a saturated aqueous sodium bicarbonate solution, then with water until neutral, dried over anhydrous magnesium sulfate, filtered, and concentrated to yield 13.96 g (86%) of white solid. Recrystallization from diisopropylether gave a white crystalline S-Methyl-N-[N'-(N''-methyl-N''-(t-butoxycarbonyl)aminosulfenyl)-N'-methylcarbamoyloxy]thioacetimidate, m.p. 96.5°–98.0° C.

Anal. Calcd for $C_{11}H_{21}N_3O_4S_2$: C, 40.85; H, 6.55; N, 12.99. Found: C, 40.92; H, 6.45; N, 13.00.

EXAMPLE IV

Preparation of
S-Methyl-N-[N'-(N''-Methyl-N''-(2-Ethylhexyloxycarbonyl)Aminosulfenyl)N'-Methylcarbamoyloxy]Thioacetimidate A solution of 14.7 g (0.05 mole) of N-(N'-2-ethylhexyloxycarbonyl-N'-methylaminosulfenyl)-N-methylcarbamoyl fluoride, 5.25 g (0.05 mole) of 1-methythioacetaldoxime and 6.07 g (0.06 mole) of triethylamine in 200 ml of 1,4-dioxane was stirred at ambient temperature for 48 hr. The mixture was then poured into 800 ml of water and extracted with four 150 ml portions of ethylacetate. The combined ethylacetate extracts were washed with 100 ml of 5% sodium hydroxide, then with water until neutral, dried over anhydrous magnesium sulfate, filtered, and concentrated to give 16.34 g (86%) of S-Methyl-N-[N'-(N''-methyl-N''-(2-ethylhexyloxycarbonyl)aminosulfenyl)N'-methylcarbamoyloxy]thioacetimidate as a yellow oil. A small amount was purified further by passing through a silica gel packed column twice to give a light yellow oil as product.

Anal. Calcd for $C_{15}H_{29}N_3O_4S_2$: C, 47.47; H, 7.70; N, 11.07. Found: C, 47.76; H, 7.78; N, 10.99.

EXAMPLE V

Preparation of S-Methyl-N-[N'-(N''-Methyl-N''-(n-Dodecyloxycarbonyl)Aminosulfenyl)N'-Methylcarbamoyloxy]Thioacetimidate A solution of 17.5 g (0.05 mole) of N-(N'-n-dodecyloxycarbonyl-N' methylaminosulfenyl)-N-methylcarbamoyl fluoride, 5.25 g (0.05 mole) of 1-methylthioacetaldoxime and 6.07 g (0.06 mole) of triethylamine in 200 ml of 1,4-dioxane was stirred at ambient temperature for 72 hr. The mixture was then poured into 800 ml of water and extracted with four 150 ml of ethylacetate. The combined ethyl acetate extracts were washed with 100 ml of 5% sodium hydroxide, then with water until neutral, dried over anhydrous magnesium sulfate, filtered, and concentrated to give 19.03 g (87%) of light tan solid. Recrystallization from diisopropyl ether yielded white crystalline solid S-Methyl-N-[N'-(N''-methyl-N''-(n-dodecyloxycarbonyl)aminosulfenyl)-N'-methylcarbamoyloxy]thioacetimidate, m.p. 64°–66° C.

Anal. Calcd for $C_{19}H_{37}N_3O_4S_2$: C, 52.38; H, 8.56; N, 9.65. Found: C, 52.66; H, 8.60; N, 9.65.

EXAMPLE VI

Preparation of S-Methyl-N-[N'-(N''-Methyl-N''-(2-Methoxyethoxycarbonyl)Aminosulfenyl)-N'-Methylcarbamoyloxy]-Thioacetimidate A solution of 14.4 g (0.06 mole) of N-(N'-2-methoxyethoxycarbonyl-N'-methylaminosulfenyl)-N-methylcarbamoyl fluoride, 6.3 g (0.06 mole) of 1-methylthioacetaldoxime, and 7.3 g (0.072 mole) of triethylamine in 200 ml of 1,4-dioxane was stirred at ambient temperature for 5 days. The mixture was then poured into 800 ml of water and extracted with four 150 ml portions of ethylacetate. The combined ethyl acetate extracts were washed with 100 ml of 5% sodium hydroxide solution, then with water until neutral, dried over anhydrous magnesium sulfate, filtered and concentrated to give 16.02 g (82%) of light tan solid. Recrystallization from diisopropylether yielded 10.5 g white crystalline solid in two crops, m.p. 86.0°–87.0° C.

Anal. Calcd for $C_{10}H_{19}N_3O_5S_2$: C, 36.91; H, 5.88; N, 12.91. Found: C, 36.87; H, 5.97; N, 12.89.

EXAMPLE VII

Preparation of S-Methyl-N-[N'-(N''-Methyl-N''-(Benzyloxycarbonyl)Aminosulfenyl)-N'-Methylcarbamoyloxy]Thioacetimidate A solution of 13.6 g (0.05 mole) of N-(N'-benzyloxycarbonyl-N'-methylaminosulfenyl)-N-methylcarbamoyl fluoride, 5.25 g (0.05 mole) of 1-methylthioacetaldoxime and 5.06 g (0.06 mole) of triethylamine in 200 ml of 1,4-dioxane was stirred at ambient temperature for 72 hr. The mixture was then poured into 800 ml of water and extracted with four 150 ml portions of ethylacetate. The combined ethylacetate extracts were washed with 100 ml of 5% sodium hydroxide solution, then with water until neutral, dried over anhydrous magnesium sulfate, filtered, and concentrated to give 16.11 g (90%) yellow oil. The crude product was purified by dissolving in 300 ml of warm diisopropylether, followed by a treatment of charcoal, filtered, and concentrated. Crystals dropped out in two crops to yield 7.94 g (44%) of S-Methyl-N-[N'-(N''-methyl-N''-(benzyloxycarbonyl)aminosulfenyl)-N'-methylcarbamoyloxy]thioacetimidate, m.p. 82°–83° C.

Anal. Calcd for $C_{14}H_{19}N_3O_4S_2$: C, 47.04; H, 5.36; N, 11.76. Found: C, 46.92; H, 5.34; N, 11.75.

EXAMPLE VIII

Preparation of S-2-Cyanoethyl-N-[[N'-[N''-Methyl-N''-(Ethoxycarbonyl)Aminosulfenyl]-N'-Methylcarbamoyloxy]]Thioacetimidate To a solution of 5.77 g (0.04 mole) of 2-cyanoethylthio acetaldoxime and 4.45 g (0.044 mole) of triethylamine in 200 ml of 1,4-dioxane was added another solution made up of 8.41 g (0.04 mole) of N-(N'-ethoxycarbonyl-N'-methylaminosulfenyl)-N-methylcarbamoyl fluoride in 30 ml of 1,4-dioxane. The temperature was held at 39° to 43° C. during the addition. The mixture was stirred for 4 hr. and then poured into 400 ml of water. The aqueous mixture was extracted with three portions of 100 ml ethyl acetate. The combined ethyl acetate extracts was washed with 100 ml of saturated aqueous sodium bicarbonate, three 100 ml portions of water, dried over anhydrous magnesium sulfate, filtered and concentrated to give 15 g crude product. Recrystallization from diisopropyl ether gave 9.03 g (68%) of S-2-Cyanoethylthio-N-[[N'-[N''-methyl-N''-(Ethoxycarbonyl)aminosulfenyl]-N'-Methylcarbamoyloxy]]-thioacetimidate, mp 80° to 82° C.

Anal. Calcd for $C_{11}H_{18}N_4O_4S_2$: C, 39.51; H, 5.43; N, 16.75. Found: C, 39.35; H, 5.33; N, 16.62.

EXAMPLE IX

Preparation of 2-[[O-[N-Methyl-N-(N'-Methyl-N'-(Ethoxycarbonylaminosulfenyl)Carbamoyl]Oximino]]-1,4-Dithiane A solution of 3.0 g (0.02 mole) of 2-oximino-1,4-dithiane, 4.2 g (0.02 mole) of N-(N'-ethoxycarbonyl-N'-methylaminosulfenyl)-N-methyl carbamoyl fluoride and 2.2 g (0.022 mole) of triethylamine in 100 ml of 1,4-dioxane was stirred at ambient temperature for 16 hr. and then poured into 400 ml of water. The aqueous mixture was extracted with three 100 ml portions of ethylacetate and then the ethyl acetate extracts were washed with 100 ml of saturated sodium bicarbonate solution, and then with water until neutral, dried over anhydrous magnesium sulfate, filtered and concentrated to yield 7.0 g residue. Recrystallization from diisopropyl ether gave 5.4 g (80%) of 2-[[O-[N-Methyl-N-[N'-methyl-N'-(ethoxycarbonylaminosulfenyl)carbamoyl]oximino]]-1,4-dithiane, m.p. 89°–91° C.

Anal. Calcd for $C_{10}H_{17}N_3O_4S_3$: C, 35.38; H, 5.05; N, 12.38. Found: C, 35.47; H, 5.11; N, 12.35.

EXAMPLE X

Preparation of 5-Methyl-4-[[O-[N-Methyl-N-[N'-Methyl-N'-(Ethoxycarbonylaminosulfenyl)Carbamoyl]Oximino]]-1,3-Oxathiolane A solution 6.66 g (0.05 mole) of 5-methyl-4-oximino-1,3-oxathiolane, 10.5 g (0.05 mole) of N-(N'-ethoxycarbonyl-N'-methylaminosulfenyl)-N-methyl carbamoyl fluoride and 5.57 g (0.055 mole) of triethylamine in 200 ml of 1,4-dioxane was stirred at 42°–45° C. for 2 hr. and at ambient temperature for 16 hr. The mixture was then poured into 400 ml of water and was extracted with four 200 ml portions of ethyl acetate. The combined ethyl acetate extracts were washed with 100 ml of saturated aqueous sodium bicarbonate, then with water until neutral, dried over anhydrous magnesium sulfate, filtered and concentrated to give 15.2 g residue. Recrystallization of the solid residue from diisopropyl ether gave 5.75 g of 5-Methyl-4-[[O-[N-Methyl-N-[N'-Methyl-N'-(Ethoxycarbonylaminosulfenyl)carbamoyl]oximino]]-1,3-oxathiolane, mp. 54°–56° C.

Anal. Calcd for $C_{10}H_{17}N_3O_5S_2$: C, 37.14; H, 5.30; N, 12.99. Found: C, 37.21; H, 5.31; N, 12.94.

EXAMPLE XI

Preparation of S-Methyl-N-[N'-(N''-Methyl-N''-(Methoxycarbonyl)Aminosulfenyl)-N'-Methylcarbamoyloxy]Thioacetimidate A quantity of 2.02 g (0.02 mole) of triethylamine was added to a solution of 2.69 g (0.01 mole) of S-Methyl-N-[N'-(N''-(fluorocarbonyl)-N''-methylaminosulfenyl)-N'-methylcarbamoyloxy]thioacetimidate and 0.96 g (0.02 mole) of anhydrous methanol in 100 ml of toluene. The reaction mixture was stirred overnight, washed with water, a saturated aqueous solution of ammonium chloride, then with water until neutral. After drying with anhydrous magnesium sulfate, the mixture was filtered, and concentrated to give 1.55 g solid. Recrystallization from diisopropyether yielded 0.83 g of S-methyl-N-[N'-(N''-methyl-N''-(methoxycarbonyl)aminosulfenyl)-N'-methylcarbamoyloxy]thioacetimidate, m.p. 83°–84° C.

Anal. Calc'd for $C_8H_{15}N_3O_4S_2$: C, 34.15; H, 5.37; N, 14.93. Found: C, 34.17; H, 5.36; N, 14.79.

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (Aphis fabae Scop.) reared on potted dwarf nasturtium plants at 65°–70° F. and 50–70 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (Spodoptera eridania, (Cram.)), reared on Tendergreen bean plants at a temperature of 80°±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F., and 50±5 percent relative humidity, were the test insects.

The test compounds were formulated by diluting the stock suspension with water to give a suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialties Manufacturing Association (Blue Book, McNair-Dorland Co., N.Y. 1954; pages 243-244, 261) under controlled conditions of 80°±°F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig, air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds at the indicated dosage rate against aphid, mite, Southern Armyworm, Bean Beetle and house fly was rated as follows:

A=excellent control
B=partial control
C=inactive or essentially no control at 500 ppm.
Dashes indicate no test conducted.

Phytotoxicity Test

Experiments were also conducted to determine the phytotoxicity of representative compounds with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Mammalian Toxicity

Certain compounds were also evaluated to determine their peroral toxicity to mammals by conventional methods. The representative animal selected for this experiment was the rat. The test results obtained are expressed in terms of the number of milligrams of composition per kilogram of weight of the animal required to achieve a mortality rate of 50 percent ($LD_{50}$).

The results of these experiments are also summarized in Table I below.

TABLE I

| Example | Compound | Insect Toxicity | | | | | A.O.RAT | Phytotoxicity | | | | | |
|---|---|---|---|---|---|---|---|---|---|---|---|---|---|
| | | Aphid | Mite | SAW | MBB | FLY | mg/Kg | Bean | Corn | Tom. | Cott. | Soy |
| I | $CH_3-S-C(CH_3)=N-O-C(=O)-N(CH_3)-S-N(CH_3)-C(=O)-OCH_2CH_3$ | A | B | A | A | A | 226 | 2 | 2 | 2 | 2 | 2 |
| II | $CH_3-S-C(CH_3)=N-O-C(=O)-N(CH_3)-S-N(CH_3)-C(=O)-O-n\text{-}Bu$ | A | B | A | A | A | — | 1 | 1 | 1 | 1 | 1 |
| III | $CH_3-S-C(CH_3)=N-O-C(=O)-N(CH_3)-S-N(CH_3)-C(=O)-O-t\text{-}Bu$ | A | C | A | A | A | 226 | 1 | 1 | 1 | 1 | 1 |
| IV | $CH_3-S-C(CH_3)=N-O-C(=O)-N(CH_3)-S-N(CH_3)-C(=O)-O-CH_2-CH(CH_2CH_3)-(CH_2)_3CH_3$ | A | B | A | A | A | — | 2 | 2 | 2 | 2 | 2 |
| V | $CH_3-S-C(CH_3)=N-O-C(=O)-N(CH_3)-S-N(CH_3)-C(=O)-O-n\text{-}C_{12}H_{25}$ | A | C | A | A | A | >640 | 1 | 1 | 1 | 1 | 1 |
| VI | $CH_3-S-C(CH_3)=N-O-C(=O)-N(CH_3)-S-N(CH_3)-C(=O)-OCH_2CH_2OCH_3$ | A | B | A | A | A | 113 | 2 | 1 | 2 | 2 | 2 |

TABLE I-continued

| Example | Compound | Insect Toxicity Aphid | Mite | SAW | MBB | FLY | A.O.RAT mg/Kg | Phytotoxicity Bean | Corn | Tom. | Cott. | Soy |
|---|---|---|---|---|---|---|---|---|---|---|---|---|
| VII | CH₃−S−C(CH₃)=N−O−C(O)−N(CH₃)−S−N(CH₃)−C(O)−OCH₂Ph | A | C | A | A | A | 113 | 2 | 2 | 2 | 2 | 2 |
| VIII | NCCH₂CH₂S−C(CH₃)=N−O−C(O)−N(CH₃)−S−N(CH₃)−C(O)−OCH₂CH₃ | A | A | A | A | A | 20 | 1 | 1 | 1 | 1 | 1 |
| IX | (dithiane)=N−O−C(O)−N(CH₃)−S−N(CH₃)−C(O)−OCH₂CH₃ | A | A | | A | A | 28.3 | 1 | 1 | 1 | 3 | 1 |
| X | CH₃CH(oxathiolane)−C=N−O−C(O)−N(CH₃)−S−N(CH₃)−C(O)−O−CH₂CH₃ | A | A | A | A | A | 18 | 1 | 1 | 2 | 1 | 2 |
| — | CH₃S−C(CH₃)=N−O−C(O)−N(CH₃)−S−N(CH₃)−C(O)−OCH(CH₃)−OCH₃ | A | A | A | A | A | — | — | — | — | — | — |
| — | CH₃S−C(CH₃)=N−O−C(O)−N(CH₃)−S−N(CH₃)−C(O)−(OCH₂CH₂)₂OCH₃ | A | A | A | A | A | — | 1 | 1 | 1 | 2 | 2 |
| — | CH₃S−C(CH₃)=N−O−C(O)−N(CH₃)−S−N(CH₃)−C(O)−(OCH₂CH₂)₃OCH₃ | A | A | A | A | A | 226.0 | 1 | 1 | 1 | 2 | 2 |

It will be understood that the insect species and other pests employed in the above tests are merely representative of a wide variety of pests that can be controlled by use of the novel compounds of this invention.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylen oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds.

What is claimed is:

1. A compound of the formula:

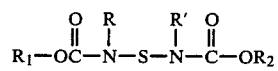

wherein:

R and R' are individually alkyl radicals having from 1 to 4 carbon atoms;

$R_1$ is: naphthyl, benzothienyl, benzofuranyl or:

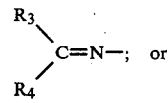

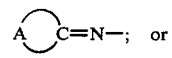

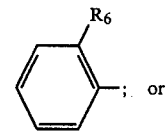

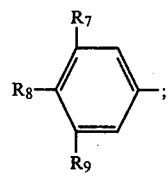

$R_2$ is other than $R_1$ and is a substituted or unsubstituted alkyl, cycloalkyl, phenylalkyl, naphthylalkyl or a heterocycloalkyl group, wherein the heterocyclic moiety is a five- or six-member ring which includes in any combination, one or two oxygen, sulfur, sulfinyl or sulfonyl groups and which may also include one divalent, amino, alkylamino or carbonyl group; wherein the permissible substituents on said groups are one or more halogen, nitrile, nitro, alkyl, alkylthio, alkylsulfinyl, alkylsulfonyl, alkoxy, alkoxycarbonylamino, or alkylcarbonylamino groups in any combination, or $R_2$ is alkoxyalkyleneoxyalkyl, alkoxy(dialkyleneoxy)alkyl or alkoxy(trialkyleneoxy)alkyl; with the proviso that except where $R_2$ is alkyl, no single alkyl or alkylene moiety in any $R_2$ group may include more than six carbon atoms;

$R_3$ is hydrogen, alkyl, alkylthio or cyano;

$R_4$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or $R_4$ is phenyl, aminocarbonyl, alkylaminocarbonyl, dialkylaminocarbonyl or a $R_5CONH-$ or $R_5CON$(alkyl)- group, where $R_5$ is hydrogen, alkyl, alkoxy or alkylthio; and A is a divalent aliphatic chain, completing a five or six member ring, which includes in any combination, one or two oxygen, sulfur, sulfinyl or sulfonyl groups and which may also include one divalent amino, alkylamino or carbonyl group;

R6 is alkoxy, alkylthio, alkyl, alkylthioalkyl, 2-dioxolanyl or halogen;

R7 is alkyl;

R8 is hydrogen, alkyl, halogen, alkylthio, alkylsulfinyl, alkylsulfonyl, alkoxy, dialkylamino, formylamino, alkylcarbonylamino, alkoxycarbonylamino or dialkylaminomethyleneimino;

R9 is hydrogen or alkyl; with the proviso that the number of aliphatic carbon atoms in R3, R4, A, R6, R7, R8 and R9, individually, may not exceed eight.

2. A compound according to claim 1 wherein R and R' are methyl.

3. A compound according to claim 1 wherein R1 is:

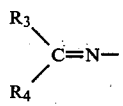

4. A compound according to claim 1 wherein R1 is:

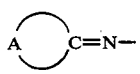

5. A compound according to claim 1 wherein R1 is:

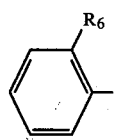

6. A compound according to claim 2 wherein R1 is:

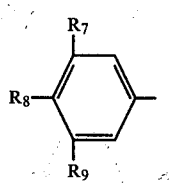

7. A compound according to claim 1 wherein R2 is alkyl having from 4 to 18 carbon atoms.

8. A compound according to claim 3 wherein R3 is methyl.

9. A compound according to claim 3 wherein R3 is ethyl.

10. A compound according to claim 3 wherein R4 is methylthio, ethylthio or propylthio.

11. A compound according to claim 3 wherein R4 is cyanomethylthio, cyanoethylthio or cyanopropylthio.

12. A compound according to claim 3 wherein R3 is methyl or ethyl and R4 is alkylthio or cyanoalkylthio.

13. A compound of the formula

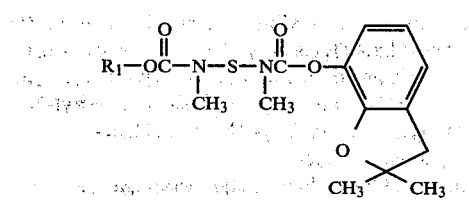

wherein R1 is ethyl or t-butyl.

14. A compound of the formula:

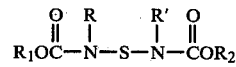

wherein:

R and R' are individually alkyl radicals having from 1 to 4 carbon atoms;

R1 is

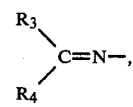

wherein:

R3 is hydrogen, alkyl or alkylthio;

R4 is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R4 is phenyl, aminocarbonyl, alkylaminocarbonyl, dialkylaminocarbonyl or a R5CONH- or R5CON(alkyl)- group where R5 is hydrogen, alkyl, alkoxy or alkylthio;

R2 is a substituted or unsubstituted alkyl, cycloalkyl, phenylalkyl or naphthylalkyl wherein the permissible substituents are one or more halogen, nitro, alkyl, alkylthio, alkylsulfinyl, alkylsulfonyl, alkoxy, alkoxy-carbonylamino or alkylcarbonylamino groups in any combination, or R2 is alkoxyalkylene-oxyalkyl, alkoxyl(dialkyleneoxy)alkyl; with the proviso that:

A. except where R2 is alkyl, no single alkyl or alkylene moiety in any R2 group may include more than six carbon atoms; and B. R3 and R4 groups individually may not include more than eight aliphatic carbon atoms.

15. A compound of the formula:

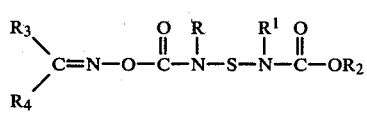

wherein:

R and R¹ were individually alkyl radical having 1 to 4 carbon atoms;

R2 is alkyl;

R3 is hydrogen or alkyl, and

R4 is alkylthio.

16. S-Methyl-N-[N'-(N''-methyl-N''-butoxycarbonyl)aminosulfenyl)-N'-methylcarbamoyloxy]thioacetimidate.

17. S-Methyl-N-[N'-(N''-methyl-N''-(t-butoxycarbonyl)aminosulfenyl)-N'-methylcarbamoyloxy]thioacetimidate.

18. S-Methyl-N-[N'-(N''-methyl-N''-(n-dodecyloxycarbonyl)aminosulfenyl)N'-methylcarbamoyloxy]thioacetimidate.

19. An insecticidal and miticidal composition which comprises an acceptable carrier and an insecticidally and miticidally effective amount of a compound of the formula:

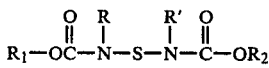

wherein:
R and R' are individually alkyl radicals having from 1 to 4 carbon atoms;
$R_1$ is: naphthyl, benzothienyl, benzofuranyl or:

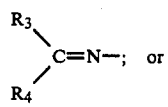

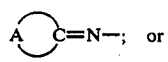

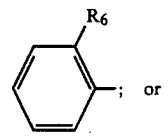

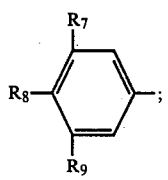

$R_2$ is other than $R_1$ and is a substituted or unsubstituted alkyl, cycloalkyl, phenylalkyl, naphthylalkyl or a heterocycloalkyl group wherein the heterocyclic moiety is a five- or six-member ring which includes in any combination, one or two oxygen, sulfur, sulfinyl or sulfonyl groups and which may also include one divalent amino, alkylamino or carbonyl group; wherein the permissible substituents on said groups are one or more halogen, nitrile, nitro, alkyl, alkylthio, alkylsulfinyl, alkylsulfonyl, alkoxy, alkoxycarbonylamino, or alkylcarbonylamino groups in any combination, or $R_2$ is alkoxyalkyleneoxyalkyl, alkoxy(dialkyleneoxy)alkyl or alkoxy(trialkyleneoxy)alkyl; with the proviso that except where $R_2$ is alkyl, no single alkyl or alkylene moiety in any $R_2$ group may include more than six carbon atoms;

$R_3$ is hydrogen, alkyl, alkylthio or cyano;

$R_4$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl, groups or $R_4$ is phenyl, aminocarbonyl, alkylaminocarbonyl, dialkylaminocarbonyl or a $R_5$CONH- or $R_5$CON(alkyl)- group, where $R_5$ is hydrogen, alkyl, alkoxy or alkylthio; and A is a divalent aliphatic chain, completing a five or six member ring, which includes in any combination, one or two oxygen, sulfur, sulfinyl or sulfonyl groups and which may also include one divalent amino, alkylamino or carbonyl group;

$R_6$ is alkoxy, alkylthio, alkyl, alkylthioalkyl, 2-dioxolanyl or halogen;

$R_7$ is alkyl;

$R_8$ is hydrogen, alkyl, halogen, alkylthio, alkylsulfinyl, alkylsulfonyl, alkoxy, dialkylamino, formylamino, alkylcarbonylamino, alkoxycarbonylamino or dialkylaminomethyleneimino;

$R_9$ is hydrogen or alkyl; with the proviso that the number of aliphatic carbon atoms in $R_3$, $R_4$, A, $R_6$, $R_7$, $R_8$ and $R_9$, individually, may not exceed eight.

20. A composition according to claim 19 wherein R and R' are methyl.

21. A composition according to claim 19 wherein $R_1$ is:

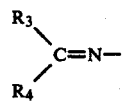

22. A composition according to claim 19 wherein $R_1$ is:

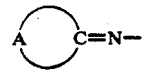

23. A composition according to claim 19 wherein $R_1$ is:

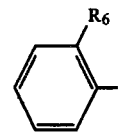

24. A composition according to claim 19 wherein $R_1$ is:

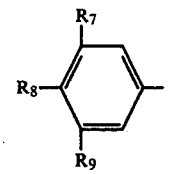

25. A composition according to claim 19 wherein $R_2$ is alkyl having from 4 to 30 carbon atoms.

26. A composition according to claim 21 wherein $R_3$ is methyl.

27. A composition according to claim 21 wherein $R_3$ is ethyl.

28. A composition according to claim 21 wherein $R_4$ is methylthio, ethylthio or propylthio.

29. A composition according to claim 21 wherein $R_4$ is cyanomethylthio, cyanoethylthio or cyanopropylthio.

30. A composition according to claim 21 wherein $R_3$ is methyl or ethyl and $R_4$ is alkylthio or cyanoalkylthio.

31. A composition according to claim 19 wherein said compound is S-2-Cyanoethyl-N-[[N'-[N'''-methyl-N''-(ethoxycarbonyl)aminosulfenyl]-N'-methylcarbamoyloxy]]thioacetimidate.

32. An insecticidal and miticidal composition which comprises an acceptable carrier and an insecticidally and miticidally effective amount of a compound of the formula:

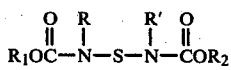

wherein:
R and R' are individually alkyl radicals having from 1 to 4 carbon atoms;
R₁ is

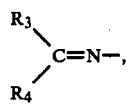

wherein:
R₃ is hydrogen, alkyl, or alkylthio;
R₄ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R₄ is phenyl, aminocarbonyl, alkylaminocarbonyl, dialkylaminocarbonyl or a R₅CONH- or R₅CON(alkyl)- group where R₅ is hydrogen, alkyl, alkoxy or alkylthio;
R₂ is a substituted or unsubstituted alkyl, cycloalkyl, phenylalkyl or naphthylalkyl wherein the permissible substituents are one or more halogen, nitro, alkyl, alkylthio, alkylsulfinyl, alkylsulfonyl, alkoxy, alkoxycarbonylamino, or alkylcarbonylamino groups in any combination, or R₂ is alkoxyalkyleneoxyalkyl, alkoxy(dialkyleneoxy)alkyl; with the proviso that:
A. except where R₂ is alkyl, no single alkyl or alkylene moiety in any R₂ group may include more than six carbon atoms; and
B. R₃ and R₄ groups individually may not include more than eight aliphatic carbon atoms.

33. A composition according to claim 32 wherein said compound is S-Methyl-N-[N'-(N''-methyl-N'''-butoxycarbonyl)aminosulfenyl)-N'-methylcarbamoyloxy]thioacetimidate.

34. A composition according to claim 32 wherein said compound is S-Methyl-N-[N'-(N''-methyl-N'''-(t-butoxycarbonyl)aminosulfenyl)-N-'-methylcarbamoyloxy]-thioacetimidate.

35. A composition according to claim 32 wherein said compound is S-Methyl-N-[N'-(N''-methyl-N'''-(n-dodecyloxycarbonyl)aminosulfenyl)N'-methylcarbamoyloxy]thioacetimidate.

36. A method of controlling insects and mites which comprises subjecting them to a miticidally or insecticidally effective amount of a compound of the formula:

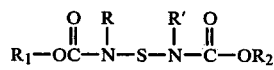

wherein:
R and R' are individually alkyl radicals having from 1 to 4 carbon atoms;
R₁ is naphthyl, benzothienyl, benzofuranyl or:

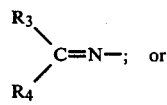

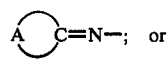

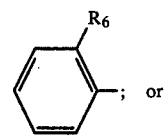

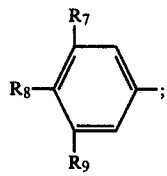

R₂ is other than R₁ and is a substituted or unsubstituted alkyl, cycloalkyl, phenylalkyl, naphthylalkyl or a heterocycloalkyl group wherein the heterocyclic moiety is a five-or six-member ring which includes in any combination, one or two oxygen, sulfur, sulfinyl or sulfonyl groups and which may also include one divalent amino, alkylamino or carbonyl group; wherein the permissible substituents on said groups are one or more halogen, nitrile, nitro, alkyl, alkylthio, alkylsulfinyl, alkylsulfonyl, alkoxy, alkoxycarbonylamino, or alkylcarbonylamino groups in any combination, or R₂ is alkoxyalkyleneoxyalkyl, alkoxy(dialkyleneoxy)alkyl or alkoxy(trialkyleneoxy)alkyl; with the proviso that except where R₂ is alkyl, no single alkyl or alkylene moiety in any R₂ group may include more than six carbon atoms;

R₃ is hydrogen, alkyl, alkylthio or cyano;
R₄ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxyaminocarbonyl, alkylaminocarbonyl, or dialkylaminocarbonyl groups or R₄ is phenyl, aminocarbonyl, alkylaminocarbonyl, dialkylaminocarbonyl or a R₅CONH- or R₅CON(alkyl)- group, where R₅ is hydrogen, alkyl, alkoxy or alkylthio; and A is a divalent aliphatic chain, completing a five or six member ring, which includes in any combination, one or two oxygen, sulfur, sulfinyl or sulfonyl groups and which may also include one divalent amino, alkylamino or carbonyl group;

R₆ is alkoxy, alkylthio, alkyl, alkylthioalkyl, 2-dioxolanyl or halogen;
R₇ is alkyl;
R₈ is hydrogen, alkyl, halogen, alkylthio, alkylsulfinyl, alkylsulfonyl, alkoxy, dialkylamino, formylamino, alkylcarbonylamino, alkoxycarbonylamino or dialkylaminomethyleneimino;
R₉ is hydrogen or alkyl;
with the proviso that the number of aliphatic carbon atoms in R₃, R₄, A, R₆, R₇, R₈ and R₉, individually, may not exceed eight.

37. A method according to claim 36 wherein R and R' are methyl.

38. A method according to claim 36 wherein $R_1$ is:

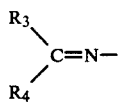

39. A method according to claim 36 wherein $R_1$ is:

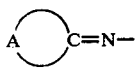

40. A method according to claim 36 wherein $R_1$ is:

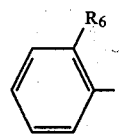

41. A method according to claim 36 wherein $R_1$ is:

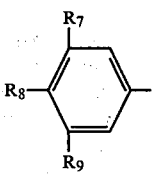

42. A method according to claim 36 wherein $R_2$ is alkyl having from 4 to 18 carbon atoms.

43. A method according to claim 38 wherein $R_3$ is methyl.

44. A method according to claim 38 wherein $R_3$ is ethyl.

45. A method according to claim 38 wherein $R_4$ is methylthio, ethylthio or propylthio.

46. A method according to claim 38 wherein $R_4$ is cyanomethylthio, cyanoethylthio or cyanopropylthio.

47. A method according to claim 38 wherein $R_3$ is methyl or ethyl and $R_4$ is alkylthio or cyanoalkylthio.

48. A method according to claim 36 wherein said compounds is S-2-Cyanoethyl-N-[[N'-[N''-methyl-N''-(ethoxycarbonyl)aminosulfenyl]-N'-methylcarbamoyloxy]]thioacetimidate.

49. A method of controlling insects and mites which comprises subjecting them to a miticidally or insecticidally effective amount of a compound of the formula:

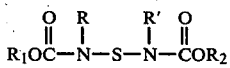

wherein:
R and R' are individually alkyl radicals having from 1 to 4 carbon atoms; $R_1$ is

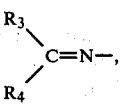

wherein:
$R_3$ is hydrogen, alkyl or alkylthio;

$R_4$ is alkyl, alkylthio, alkoxy alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or $R_4$ is phenyl, aminocarbonyl, alkylaminocarbonyl, dialkylaminocarbonyl or a $R_5CONH-$ or $R_5CON(alkyl)-$ group where $R_5$ is hydrogen, alkyl, alkoxy or alkylthio;

$R_2$ is a substituted or unsubstituted alkyl, cycloalkyl, phenylalkyl or naphthylalkyl wherein the permissible substituents are one or more halogen, nitro, alkyl, alkylthio, alkylsulfinyl, alkylsulfonyl, alkoxy, alkoxycarbonylamino, or alkylcarbonylamino groups in any combination, or $R_2$ is alkoxyalkylene-oxyalkyl, alkoxy(dialkyleneoxy)alkyl; with the proviso that:

A. except where $R_2$ is alkyl, no single alkyl or alkylene moiety in any $R_2$ group may include more than six carbon atoms; and B. $R_3$ and $R_4$ groups individually may not include more than eight aliphatic carbon atoms.

50. A method according to claim 49 wherein said compound is S-Methyl-N-[N'-(N''-methyl-N''-butoxycarbonyl)aminosulfenyl)-N'-methylcarbamoyloxy]thioacetimidate.

51. A method according to claim 49 wherein said compound is S-Methyl-N-[N'-(N''-methyl-N''-(t-butoxycarbonyl)aminosulfenyl)-N'-methylcarbamoyloxy]thioacetimidate.

52. A method according to claim 49 wherein said compound is S-Methyl-N-[N'-(N''-methyl-N''-(n-dodecyloxycarbonyl)aminosulfenyl)N'-methylcarbamoyloxy]thioacetimidate.

53. A method of preparing a compound of the formula:

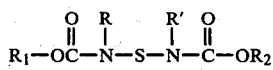

which comprises reacting a compound of the formula:

with a compound of the formula $R_2OH$; or alternatively reacting a compound of the formula:

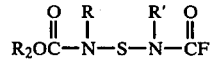

with a compound of the formula $R_1OH$ in the presence of at least one equivalent of an acid acceptor, wherein:
R nd R' are individually alkyl radicals having from 1 to 4 carbon atoms;
$R_1$ is: naphthyl, benzothienyl, benzofuranyl or:

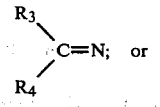

-continued

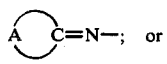; or

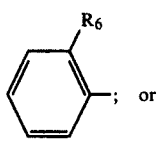; or

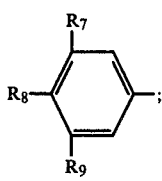;

R$_2$ is other than R$_1$ and is a substituted or unsubstituted alkyl, cycloalkyl, phenylalkyl, naphthylalkyl or a heterocycloalkyl group, wherein the heterocyclic moiety is a five-or six-member ring which includes in any combination, one or two oxygen, sulfur, sulfinyl or sulfonyl groups and which may also include one divalent, amino, alkylamino or carbonyl group; wherein the permissible substituents on said groups are one or more halogen, nitrile, nitro, alkyl, alkylthio, alkylsulfinyl, alkylsulfonyl, alkoxy, alkoxycarbonylamino, or alkylcarbonylamino groups in any combination, or R$_2$ is alkoxyalkyleneoxyalkyl, alkoxy(dialkyleneoxy)alkyl or alkoxy(trialkyleneoxy)alkyl; with the proviso that except where R$_2$ is alkyl, no single alkyl or alkylene moiety in any R$_2$ group may include more than six carbon atoms;

R$_3$ is hydrogen, alkyl, alkylthio or cyano;

R$_4$ is alkyl, alkylthio, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or R$_4$ is phenyl, aminocarbonyl, alkylaminocarbonyl, dialkylaminocarbonyl or a R$_5$CONH- or R$_5$CON(alkyl)- group, where R$_5$ is hydrogen, alkyl, alkoxy or alkylthio; and A is a divalent aliphatic chain, completing a five or six member ring, which includes in any combination, one or two oxygen, sulfur, sulfinyl or sulfonyl groups and which may also include one divalent amino, alkylamino or carbonyl group;

R$_6$ is alkoxy, alkylthio, alkyl, alkylthioalkyl, 2-dioxolanyl or halogen;

R$_7$ is alkyl;

R$_8$ is hydrogen, alkyl, halogen, alkylthio, alkylsulfinyl, alkylsulfonyl, alkoxy, dialkylamino, formylamino, alkylcarbonylamino, alkoxycarbonylamino, alkoxycarbonylamino or dialkylaminomethyleneimino;

R$_9$ is hydrogen or alkyl; with the proviso that the number of aliphatic carbon atoms in R$_3$, R$_4$, A, R$_6$, R$_7$, R$_8$ and R$_9$, individually, may not exceed eight.

54. A method of preparing a compound of the formula:

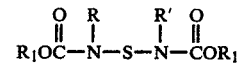

which comprises reacting a compound of the formula:

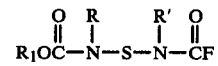

with a compound of the formula R$_2$OH; or alternatively reacting a compound of the formula:

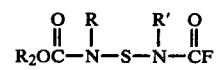

with a compound of the formula R$_1$OH in the presence of at least one equivalent of an acid acceptor wherein:
R and R' are individually alkyl radicals having from 1 to 4 carbon atoms; R$_1$ is

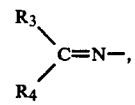

wherein:
R$_3$ is hydrogen, alkyl, or alkylthio;
R$_4$ is alkyl, alkylthio, alkoxy alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R$_4$ is phenyl, aminocarbonyl, alkylaminocarbonyl, dialkylaminocarbonyl or a R$_5$CONH- or R$_5$CON(alkyl)- group where R$_5$ is hydrogen, alkyl, alkoxy or alkylthio;
R$_2$ is a substituted or unsubstituted alkyl, cycloalkyl, phenylalkyl or naphthylalkyl wherein the permissible substituents are one or more halogen, nitro, alkyl, alkylthio, alkylsulfinyl, alkylsulfonyl, alkoxy, alkoxycarbonylamino, or alkylcarbonylamino groups in any combination, or R$_2$ is alkoxyalkyleneoxyalkyl, alkoxy(dialkyleneoxy)alkyl; with the proviso that:
A. except where R$_2$ is alkyl, no single alkyl or alkylene moiety in any R$_2$ group may include more than six carbon atoms; and
B. R$_3$ and R$_4$ groups individually may not include more than eight aliphatic carbon atoms.

* * * * *